(12) United States Patent
Finkele et al.

(10) Patent No.: US 6,459,083 B1
(45) Date of Patent: Oct. 1, 2002

(54) APPARATUS FOR DETECTING THE CONDITION OF A ROAD SURFACE

(75) Inventors: Rolf Finkele, Schelklingen; Tobias Kippenberg, Bremen; Gerd Wanielik, Freiberg; Andreas Schreck, Blaustein, all of (DE)

(73) Assignee: DaimlerChrysler AG, Stuttgart (DE)

( * ) Notice: Subject to any disclaimer, the term of this patent is extended or adjusted under 35 U.S.C. 154(b) by 0 days.

(21) Appl. No.: 09/445,626

(22) PCT Filed: Mar. 27, 1999

(86) PCT No.: PCT/DE99/00942

§ 371 (c)(1),
(2), (4) Date: Mar. 6, 2000

(87) PCT Pub. No.: WO99/53461

PCT Pub. Date: Oct. 21, 1999

(30) Foreign Application Priority Data

Apr. 9, 1998 (DE) .......................................... 198 16 004

(51) Int. Cl.$^7$ .............................................. G01N 21/55
(52) U.S. Cl. .............................. 250/339.11; 250/339.1; 324/643
(58) Field of Search ........................ 250/339.11, 339.1; 324/643

(56) References Cited

U.S. PATENT DOCUMENTS

| 5,218,206 A | 6/1993 | Schmitt et al. |
| 5,497,100 A | 3/1996 | Reiser et al. |
| 5,739,534 A | * 4/1998 | Estenson et al. ....... 250/339.11 |
| 5,962,853 A | * 10/1999 | Huth-Fehre et al. ... 250/339.11 |

FOREIGN PATENT DOCUMENTS

| DE | 36 12 550 | 10/1987 |
| DE | 38 41 333 | 6/1990 |
| DE | 40 08 280 | 9/1991 |
| DE | 40 40 842 | 2/1992 |
| DE | 41 33 359 | 4/1993 |
| DE | 42 02 691 | 8/1993 |
| DE | 43 00 896 | 4/1994 |
| DE | 195 06 550 | 8/1996 |
| DE | 196 03 557 | 8/1997 |
| EP | 0 005 696 | 12/1979 |
| EP | 0 470 506 | 2/1992 |
| WO | 85/02266 | 5/1985 |

OTHER PUBLICATIONS

W.R. Whalley, et al., "Estimation of Soil Moisture Status Using Near Infrared Reflrctance", *Hydrological Processes*, vol. 5, pp. 321–327 (1991).
Patent Abstracts of Japan, vol. 005, No. 2, Feb. 7, 1981. JP 55 147375, Nov. 17, 1980.

* cited by examiner

Primary Examiner—Constantine Hannaher
Assistant Examiner—Andrew Israel
(74) Attorney, Agent, or Firm—Kenyon & Kenyon

(57) ABSTRACT

An apparatus for recognizing road conditions, for use especially in a motor vehicle, includes an infrared transmitter-receiver system. Devices are provided which make it possible to separate signal fractions into different infrared wavelength ranges. This allows for the reliable evaluation of the conditions of the road section being monitored, using a simple and economical device. The infrared devices may be combined with a microwave device.

24 Claims, 2 Drawing Sheets

APPARATUS FOR DETECTING THE CONDITION OF A ROAD SURFACE

FIELD OF THE INVENTION

The present invention relates to an arrangement for detecting the condition of a road surface.

RELATED TECHNOLOGY

Arrangements for detecting the condition of a road surface may be an important element of vehicle traffic safety. A road surface condition that reduces vehicle tire friction on the road surface can be extremely hazardous. An urgent need therefore exists for a reliable arrangement to detect the condition of the road surface.

A surface monitoring system which can also be used to detect the condition of a road surface and which includes a microwave transceiver system with one or more operating frequencies is known from U.S. Pat. No. 5,497,100. The variable reflectivity of dry, wet, and icy road surfaces is evaluated to distinguish between different road surface conditions.

Other known systems use transceiver equipment with infrared radiation, preferably using multiple wave bands and evaluating the variable reflectivity of different road surface conditions. In German Patent Document No. 40 08 280 A1, for example, information about the road surface condition is obtained by forming the ratio of received signals detected on various wave bands. In Hydrological Processes, Vol. 5, pages 321–327,describes the use of the infrared absorption capacity of water to determine ground moisture by measuring the reflectivity of soil for different IR wavelengths.

Combining a microwave system and an infrared system is particularly advantageous, since both of these systems complement each other advantageously in terms of their ability to distinguish between different road surface conditions. German Patent Document No. 40 40 842 A1, for example describes an infrared microwave sensor system for detecting the condition of a road surface, which applies broadband IR radiation to a surface, detects backscattered light that has been separated into multiple wave bands, and also measures surface reflectivity for microwaves. A decision about the road surface condition is obtained by performing a logic operation on the different measurement signals or signals derived from them in a logic gate arrangement. A similar system is described in German Patent Document No. 196 03 557 A1 in which a first wave band with one water absorption band and a second wave band with a lower absorption by water are selected for the infrared system.

SUMMARY OF THE INVENTION

An object of the present invention is to provide an apparatus for detecting the condition of a road surface which provides reliable information about the road surface condition, while maintaining a simple and economical design and, in particular, is suitable for use in road vehicles.

The present invention provides an apparatus for detecting a condition of a road surface. The apparatus includes an infrared transmitter for emitting infrared radiation in at least a first and a second wave band so as to illuminate the road surface, the transmitter varying an intensity of the emitted radiation over time in at least the first wave band. The apparatus also includes an infrared receiver for detecting and evaluating an intensity of backscattered infrared radiation from the road surface in the first and second wave bands so as to obtain information about the condition of the road surface, the receiver correlating at least a portion of the backscattered radiation with the variation over time of the intensity of the emitted radiation in at least the first band.

By improving the distinction between the relevant signal components in the infrared receiver, the present invention provides a more precise assessment of the reflection and absorption properties of the monitored surface segment, thus supplying more accurate and more reliable information about the condition of this surface segment. Advantageously, at least on one of the different wave bands used, the intensity (transmitted power) of the IR radiation emitted on this wave band is varied over time, and a correlation of the radiated power received by the receiver, using knowledge of the variation over time of the emitted radiation intensity, improves the ability to separate the different radiation components. The variation over time of the emitted radiated power and the correlation of the received signal makes it possible, in particular, to effectively eliminate the influence of ambient light. Such devices can be achieved at little expense and also considerably improve the separate evaluation of the individual signal components. The individual means used to vary the intensity of the emitted radiation over time, which can be carried out alone or in different combinations. The design and/or circuitry needed to achieve these devices are basically known to those skilled in the art. Some of these devices have been used in different applications so that experience from other fields can be used for implementation.

The variation over time can apply to the radiation on one wave band alone, or the variation of the emitted radiation intensity can apply to both wave bands. The indication of two wave bands is not intended to exclude the possibility of using and evaluating more than two different wave bands. To provide a simple and cost-effective arrangement, however, a design with two different infrared wave bands is preferred. It has been shown that a good assessment of the condition of a road surface can be obtained with two different wave bands, in particular one wave band with a low absorption in water, for example around 950 nm, and a second wave band with a higher absorption by water (water absorption band), for example 1350 nm.

According to a first advantageous embodiment, the variation over time of the emitted radiation intensity is achieved by clocking the radiated power, in particular by switching between a turn-on power level and an emitter status with no IR power emission. Both wave bands are advantageously operated in a clock mode of this type, with the power being emitted on the two different wave bands by time-division multiplexing, and with emission pauses also being advantageously provided. Time-division multiplex clocking also makes it possible to define receiving intervals in which only the radiation of one wave band is expected as the information signal component. This makes it especially easy to separate the signal components of the different wave bands. A very long switching interval should advantageously be selected, compared to the runtime of the radiation emitted by the emitter over the illuminated surface in the receiver, making it unnecessary to additionally account for a phase shift in the clock signals. Providing emission pauses makes it possible to advantageously determine the ambient radiation component on the two useful wave bands in the receiver at such intervals and to account for this component in the illumination intervals, for example by subtracting a corresponding interference signal component and/or by influencing the working point of one or more receiving elements.

A further advantageous embodiment for achieving the variation over time of the emitted IR radiation intensity involves periodically modulating the radiated power. The intensities on both wave bands are preferably modulated at different modulation frequencies, and the signal components in the receiver separated from each other and from an interference signal component by frequency-discriminating demodulation, for example by synchronous rectification or bandpass filtration. A high-frequency modulation is preferably carried out, for example, in the 10–100 kHz range. Modulating the intensities on both wave bands, using different modulation frequencies, makes it possible to emit, receive, and evaluate signals on both wave bands simultaneously so that equal time segments, and thus backscattering from the same surface segments, can be processed and evaluated through comparison.

Another advantageous means for varying the intensity over time is the pulsed emission of IR radiation, advantageously selecting the length, sequencing time and similar quantities of the on and off pulses according to a pulse code pattern that is known per se and separating the signal components on the receiver side by correlation with compression filters or similar devices in a manner that is known per se. In this case as well, the radiation can be emitted on both wave bands simultaneously using variable pulse coding for different wave bands. In an especially advantageous manner, the emitter elements of the transmitter can be LEDs or laser diodes. Diodes of this type can be obtained economically, require little space for installation, and can be easily controlled electrically. Emitter diodes for the two preferred wave bands are known per se. A first embodiment provides two separate emitter elements for the two wave bands used. However, it is also possible to use a shared emitter element that can be controlled to emit separately on two wave bands. Moreover, a shared broadband radiating emitter element can be provided for emitting the radiation, with a distinction between the wave bands being made by wavelength-discriminating filters for the two wave bands in the radiation path.

If separate emitter elements are used for the different wave bands, they must be separate emitter elements that are preferably controlled by separate electrical signals from a controller, clock generators, or similar devices. If a broadband radiating emitter element is used, the intensity of the radiated power can be varied on one or both wave bands by controllable light valves in the radiation path, for example controllable liquid crystal windows. The wavelength filters can be structurally combined with the controllable light valves. A conventional thermal IR radiator can also be used as the radiation element.

For the different wave bands of the radiation to be detected, the receiver preferably includes separate receiving elements whose wavelength discriminating capacity is either preferably provided by the material composition of semiconductor receiving elements or by upstream wavelength-discriminating filters. However, the variation over time of the radiated power intensity also allows a shared broadband receiving element to be used for both wave bands, due to the corresponding evaluation accounting for this variation, in which case the separation of the different radiation components is transferred to a downstream electronic evaluator, for example one with discrete mounted filters or similar components and/or a digital signal processing system. In particular, photodiodes which provide advantageous devices for easily setting the working point, for example as a function of a detected ambient radiation level, are suitable as receiving elements in the receiver.

The transmitter and receiver in the IR evaluator circuit are preferably structurally combined for both wave bands and form a monostatic arrangement, ie., the transmitter and receiver are located basically in the same place. The directed emission of IR transmitted power and the receipt of backscattered radiation preferably take place within a 0° to 30° angle toward the normal of the monitored surface. In the preferred use in a motor vehicle, a surface segment located beneath the arrangement is illuminated and monitored.

An arrangement in which the IR transceiver equipment described above is operated in combination with an additional microwave transceiver is particularly advantageous, in which case the evaluation means, which are known per se, allow an especially reliable distinction to be made between the relevant road surface conditions. When used in road vehicles, the transmitted power of the microwave equipment can also be varied over time, making it possible to reduce or eliminate mutual interference of similar arrangements installed in separate vehicles.

The sensors, in particular the microwave sensors—and also, in part, the emitters—can be dependent on temperature, which can influence the measurement results. To eliminate errors of this type, temperature sensors are advantageously provided on or near components that are greatly dependent on temperature. A digital signal processing system is advantageously used to correct the measurement signals according to the measured temperatures.

According to a further embodiment of the present invention, the measured values determined in the receiver and relating to radiation components on the different wave bands can be supplied to a classifier as input quantities to select one of multiple road surface conditions to be determined, with this classifier making an assignment to one of multiple classes for the road surface condition. The measured values determined in the receiver are subjected to an analog/digital conversion for this purpose. The advantage of a classifier, in particular, is that the standard for assigning a class to a combination of measured values does not require explicit models to be established on the backscattering properties of certain road surface conditions, but rather the classifier can be set on the basis of training examples. In addition to the measured values relating to signal components from the two IR wave bands and possibly the additional microwave equipment, at least one measured value relating to received ambient radiation on at least one of the wave bands is preferably also supplied to the classifier as a further input quantity. A particularly useful embodiment of a classifier contains a look-up table. The measurement signals or signals derived from them are used in digital form as addresses or sub-addresses for table addressing purposes. The table contains the road surface condition classes.

Individual components of the arrangement according to the present invention can also be described in combination with further measurement systems and/or linked to the latter. For example, the measurement results of any speed sensors and outside temperature sensors that may be present can be linked to road surface condition information derived from the arrangement according to the present invention, thus obtaining a final determination. The individual components of the transmitter and receiver of the IR system as well as components of the microwave system can be implemented entirely or partially in a shared integrated circuit. In addition to wavelength separation, the polarimetric behavior of the monitored road surface can also be determined and taken into account. Upon detecting a road surface condition with poor tire adherence properties, the determination of monitored road surface condition can result, in a manner that is known per se, in the emission of optical and/or acoustic warning signals or to direct intervention in the vehicle status, for example by reducing the speed.

BRIEF DESCRIPTION OF THE DRAWINGS

The present invention is explained in greater detail below with reference to the drawings in which.

DETAILED DESCRIPTION

Figure 1:
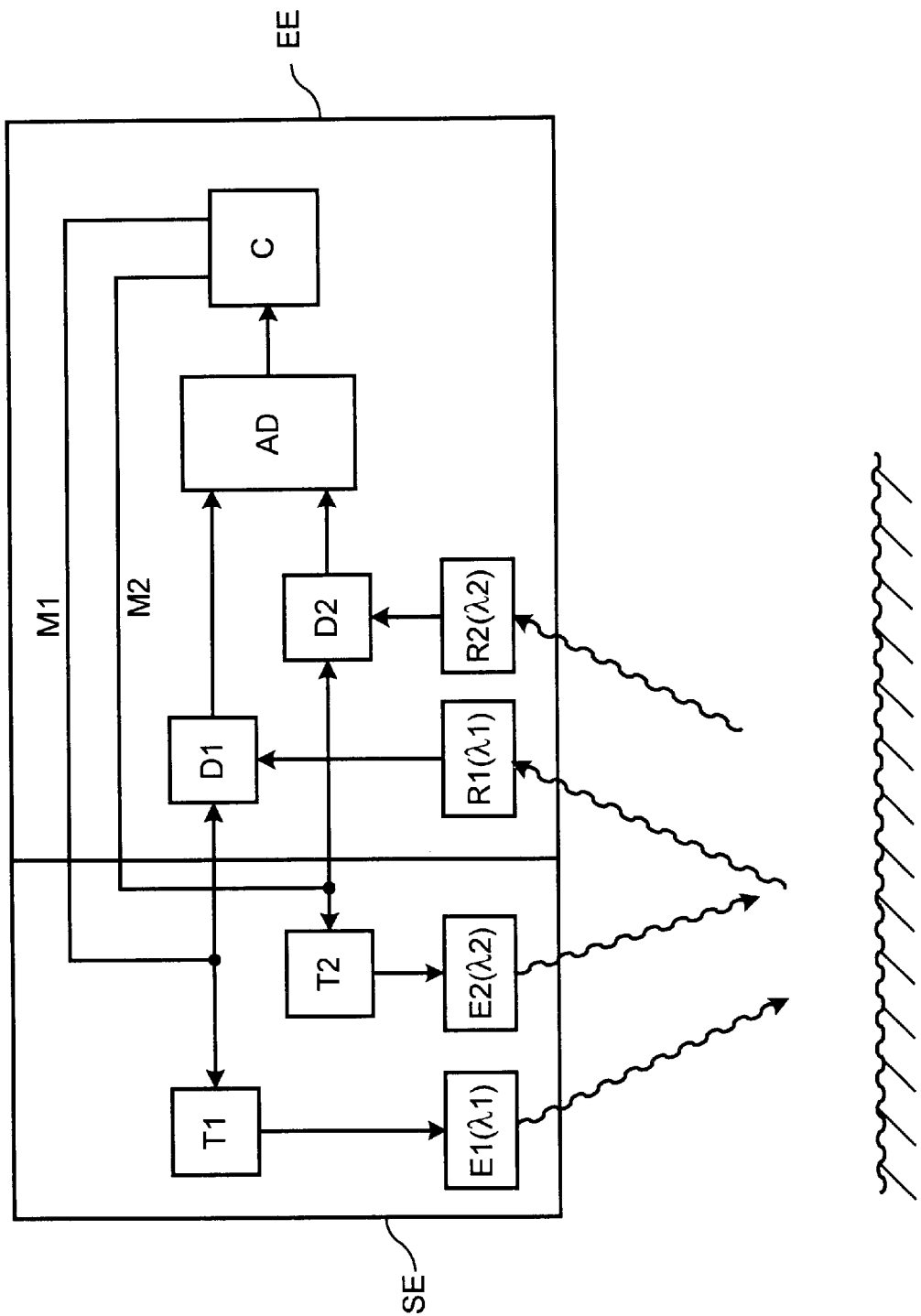
FIG. 1 shows a block diagram of a first embodiment of an apparatus for detecting the condition of a road surface according to the present invention.

The apparatus illustrated in FIG. 1 includes an infrared transmitter SE and an infrared receiver EE. Transmitter SE includes a first emitter element E1, which emits radiation on a first wave band around a first wavelength $\lambda 1$ in the direction of the surface of a road F; and a second emitter element E2, which emits radiation on a second wave band around a second wavelength $\lambda 2$ in the direction of the road surface, where, for example, $\lambda 1=950$ nm and $\lambda 2=1350$ nm. The variation over time of the intensity of the radiation emitted by the two emitter elements is controlled by two clock generators T1 and T2, respectively. In the receiver, two receiving elements, R1 for a first wave band around $\lambda 1$ and R2 for a second wave band around $\lambda 2$, detect the radiation backscattered on the road surface on a wavelength-discriminating basis. The spectral curves of emitter elements E1 and E2, respectively, and receiving elements R1 and R2, respectively, assigned by the wave band are not necessarily completely identical. In addition, the spectral curves of the separate emitter elements and/or separate receiving elements can overlap.

The radiation components detected in receiving elements R1, R2 also demonstrate a time variation in intensity corresponding to the time variation of the emitted radiation. This time variation in intensity is accounted for in demodulators D1, D2 to further reduce the interference signal components in the received signals. For example, modulation control signals M1, M2 are sent for this purpose from a controller to clock generators T1, T2 of the emitter elements as well as to demodulators D1, D2 of the receiving elements. Demodulators D1, D2 can be, for example, synchronous rectifiers, timer circuits, bandpass filters or other circuits suitable for utilizing time information. Moreover, signal components can be integrated for equalizing short-term fluctuations over a predetermined period of time.

The output signals of demodulators D1, D2 are supplied to an analog/digital converter arrangement A/D and evaluated in digital form in an evaluator circuit C, for example a processor, a user-programmable circuit or similar element. Evaluator circuit C can simultaneously serve as a control circuit for generating modulation control signals M1, M2.

Emitter elements E1, E2 and receiving elements R1, R2 are advantageously protected from the road surface by radiation-permeable windows having a dirt-resistant surface coating. The windows can also be in the form of lenses to focus the radiation.

Figure 2:
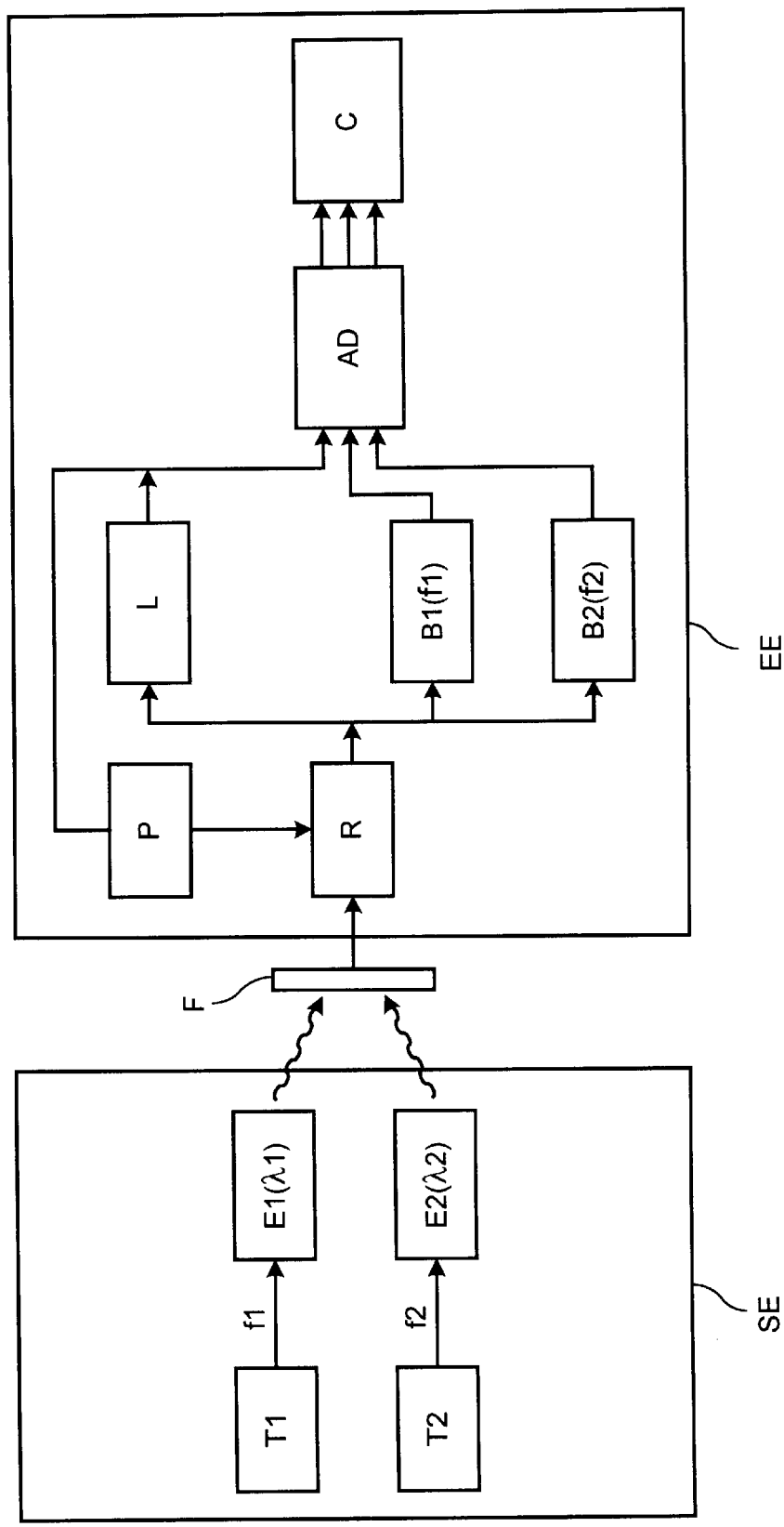
FIG. 2 shows a block diagram of a second embodiment.

In the arrangement illustrated in FIG. 2, the road surface is represented differently as a transmission element F with certain transmission properties corresponding to the road surface conditions and is located between separate emitters E1, E2 of transmitter SE and a shared broadband receiving element R in receiver EE in the radiation path. Receiving element R is, for example, a photodiode whose working point settings are performed by a controller P and can be varied. The output signal from broadband receiving element R is supplied simultaneously to a low pass L, a first bandpass filter B1, and a second bandpass filter B2. Clock generators T1, T2 in the transmitter must, in this case, modulate the intensity of the radiation emitted by emitter elements E1, E2 at different high-frequency modulation frequencies F1, F2. The center frequencies of bandpass filters B1 and B2, respectively, are adjusted to modulation frequencies F1, F2 of clock generators T1 and T2, respectively, in the transmitter and filter the backscattered signal components belonging to the different wavelengths from the electrical output signal of optical broadband detector R. Low pass L can be used to determine a value for the unmodulated ambient radiation component. This value for the ambient radiation component can be used, for example, to set and adjust the working point of shared receiving element R via working point controller P.

The output signals from low pass L, bandpass filter B1, and bandpass filter B2 are supplied to an A/D converter, which passes them on to an evaluator circuit C in digitized form.

The present invention is not limited to the embodiments described above, but rather can be varied in a number of ways according to the ability of those skilled in the art.

What is claimed is:

1. An apparatus for detecting a condition of a road surface, the apparatus comprising:

an infrared transmitter for emitting infrared radiation in at least a first and a second wave band so as to illuminate the road surface, the transmitter varying an intensity of the emitted radiation over time in at least the first wave band; and an infrared receiver for detecting and evaluating an intensity of backscattered infrared radiation from the road surface in the first and second wave bands so as to obtain information about the condition of the road surface, the receiver correlating at least a portion of the backscattered radiation with the variation over time of the intensity of the emitted radiation in at least the first band.

2. The apparatus as recited in claim 1 wherein the varying over time includes clocking the intensity of the emitted radiation in the first wave band.

3. The apparatus as recited in claim 1 wherein the varying over time includes periodic modulation of the emitted radiation in the first wave band.

4. The as recited in claim 1 wherein the varying over time includes pulse coding of the emitted radiation in the first wave band.

5. The apparatus as recited in claim 1 wherein the transmitter varies the intensity of the emitted radiation in the first and second wave bands using different respective first and second time curves.

6. The apparatus as recited in claim 5 wherein the transmitter emits radiation in the first and second wave bands using time-division multiplexing.

7. The apparatus as recited in claim 6 wherein the transmitter modulates the radiation in the first and second wave bands using different respective modulation frequencies.

8. The apparatus as recited in claim 1 wherein there are emission pauses during which the transmitter does not emit radiation.

9. The apparatus as recited in claim 8 wherein the receiver determines a value for ambient radiation in at least one of the first and second wave bands during the emission pauses.

10. The apparatus as recited in claim 9 wherein the receiver uses the value determined for the ambient radiation to set a working point of a receiving element.

11. The apparatus as recited in claim 1 wherein the transmitter includes a first and a second emitter for the first and second wave bands, respectively.

12. The apparatus as recited in claim 1 wherein the transmitter includes a shared broadband emitter for the first and second wave bands and a first and a second wavelength-discriminating filter for the first and second wave bands, respectively, the first and second wavelength-discriminating filters being disposed in a radiation path of the transmitter.

13. The apparatus as recited in claim 11 wherein the transmitter varies respective intensities of the respective radiation emitted by the first and second emitters.

14. The apparatus as recited in claim 1 wherein the transmitter includes controllable light valves in a radiation path of the transmitter.

15. The apparatus as recited in claim 1 wherein the receiver includes a first and a second receiving element for the first and second wave bands, respectively.

16. The apparatus as recited in claim 1 wherein the receiver includes a shared broadband receiving element for the first and second wave bands.

17. The apparatus as recited in claim 1 wherein the transmitter includes at least one emitting element, the at least one emitting element including at least one of an LED and a laser diode.

18. The apparatus as recited in claim 1 wherein the receiver includes at least one receiving element, the at least one receiving element including at least one photodiode.

19. The apparatus as recited in claim 1 wherein the transmitter and the receiver are disposed in a monostatic arrangement.

20. The apparatus as recited in claim 1 further comprising a microwave transceiver.

21. The apparatus as recited in claim 20 wherein a transmitted power of the microwave transceiver is varied over time.

22. The apparatus as recited in claim 1 further comprising a classifier and wherein the receiver produces measured values, an analog/digital conversion being performed on the measured values, the measured values being inputted to the classifier, the classifier making an assignment to one of multiple classes corresponding to the road surface condition.

23. The apparatus as recited in claim 22 wherein the measured values inputted to the classifier include at least measured values relating to the backscattered radiation in the first and second wave bands.

24. The apparatus according to claim 22, wherein the measured values inputted to the classifier include at least one measured value relating to the received ambient radiation.

* * * * *

UNITED STATES PATENT AND TRADEMARK OFFICE
CERTIFICATE OF CORRECTION

PATENT NO. : 6,459,083 B1
DATED : October 1, 2002
INVENTOR(S) : Rolf Finkele et al.

It is certified that error appears in the above-identified patent and that said Letters Patent is hereby corrected as shown below:

Column 1,
Line 30, before "Hydrological" delete "In";

Column 2,
Line 23, change "means" to -- devices --;
Line 24, after "time" delete ",which"; and Column 5,
Line 6, after "embodiment" insert -- of an apparatus for detecting the condition of a road surface according to the present invention --.

Signed and Sealed this

Third Day of August, 2004

JON W. DUDAS
*Acting Director of the United States Patent and Trademark Office*